United States Patent [19]

Itoi et al.

[11] Patent Number: 5,110,796
[45] Date of Patent: May 5, 1992

[54] PROPHYLACTIC AND THERAPEUTIC AGENTS FOR CATARACTS

[75] Inventors: Motokazu Itoi; Shizuko Kobayashi, both of Tokyo; Yasuo Ishii, Saitama; Minako Kasuya, Kanagawa, all of Japan

[73] Assignee: Yamanouchi Pharmaceutical Co., Ltd., Tokyo, Japan

[21] Appl. No.: 447,173

[22] Filed: Dec. 7, 1989

[30] Foreign Application Priority Data

Dec. 9, 1988 [JP] Japan ................. 63-311717

[51] Int. Cl.$^5$ ................. A61K 37/02; C07K 5/08
[52] U.S. Cl. ................. 514/18; 514/18; 514/19; 530/331
[58] Field of Search ................. 514/18, 19; 530/331

[56] References Cited

U.S. PATENT DOCUMENTS

| | | | |
|---|---|---|---|
| 4,709,013 | 11/1987 | Nagano | 530/331 |
| 4,771,036 | 9/1988 | Pigiet et al. | 514/18 |
| 4,927,808 | 5/1990 | Kitahara et al. | 530/331 |

FOREIGN PATENT DOCUMENTS 0249401  6/1987  European Pat. Off. ............ 514/18

Primary Examiner—Lester L. Lee
Assistant Examiner—S. G. Marshall
Attorney, Agent, or Firm—Burgess, Ryan & Wayne

[57] ABSTRACT

A prophylactic and therapeutic agent is provided for the prevention and treatment of cataracts. The agent is comprised of glutathione monoalkyl esters such as, isopropyl γ-L-glutamyl-L-cysteinyl glycinate sulfate, and a pharmaceutically acceptable carrier.

3 Claims, 4 Drawing Sheets

FIG. 1

| SCORING | | X-RAY IRRADIATED CONTROL | GLUTATHIONE MONOISOPROPYL ESTER (20 mg/kg) |
|---|---|---|---|
| I | ○ | — | 13 |
| II | ⊕ | — | 56 |
| III | ⊕ | — | 13 |
| IV | ⊕ | 30 | 18 |
| V | ◉◐ | 50 | — |
| VI | ● | 10 | — |
| VII | ● | 10 | — |

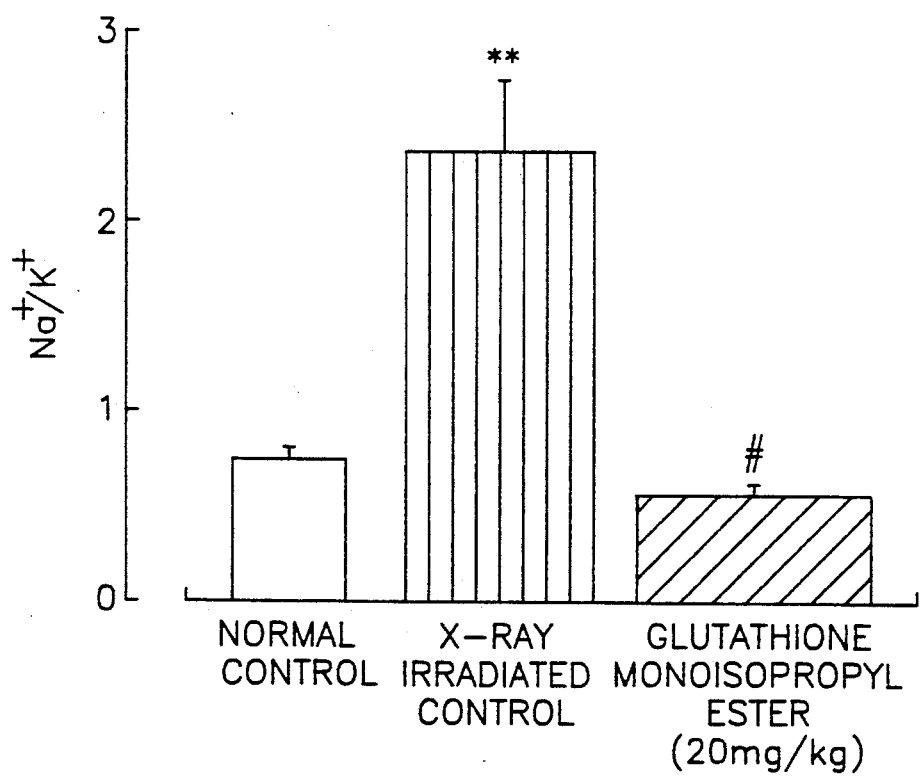

**P<0.01 (vs normal control)
P<0.05 (vs X-ray irradiated control)

PROPHYLACTIC AND THERAPEUTIC AGENTS FOR CATARACTS

BACKGROUND OF THE INVENTION

1. Field of the Invention

The present invention relates to prophylactic and therapeutic agents for cataracts and radiation-protecting agents comprising glutathione monoalkyl esters. In another aspect, the invention is directed to a method for the prevention and treatment of cataracts using the agents of this invention.

2. Description of the Related Art

Cataracts refer to a state in which the stromatic lens has decreased optical permeability caused by the generation and the deposition of certain materials, which results in the decrease of the amount of light which can reach the interior of eyes, and as a result the visual acuity is decreased.

Cataracts may be classified as congenital, senile, diabetic, complicated cataracts, and the like. The factors that cause such a state are many and X-ray radiation is but one of these factors.

As therapeutic agents for cataracts, there have been hitherto applied an operation therapy and a drug therapy such as the administration of eye-drops containing cataline or glutathione and of KI or vitamin C, and the like but the therapy except for an operation therapy have some troubles in the fundamental treatment of cataracts.

The glutathione monoalkyl esters are alkyl esters of glutathione with respect to its glycine carboxyl group. It has been found that these compounds are useful as therapeutic agents for cataracts, in particular, as therapeutic agents for cataracts induced by radioactive rays or X-ray radiation.

Also, the effect is remarkably superior to that of glutathione-containing eye-drops described above, contrary to the expectation of a person skilled in the relevant art.

SUMMARY OF THE INVENTION

In its broad aspect, the present invention relates to prophylactic and therapeutic agents for the prevention and treatment of cataracts. The invention also relates to the use of the agents for the prevention and treatment of cataracts.

The agents of the present invention are comprised of a compound of the general formula (I):

(I)

wherein R represents an alkyl group, or salts thereof, and a pharmaceutically acceptable carrier.

BRIEF DESCRIPTION OF THE DRAWINGS

FIG. 1 in a chart showing the scoring results for the lens with X-ray induced cataracts for the glutathione monoisopropyl ester sulfate group (20 mg/Kg), which is obtained with a slit lamp.

DETAILED DESCRIPTION OF THE INVENTION

Figure 2:
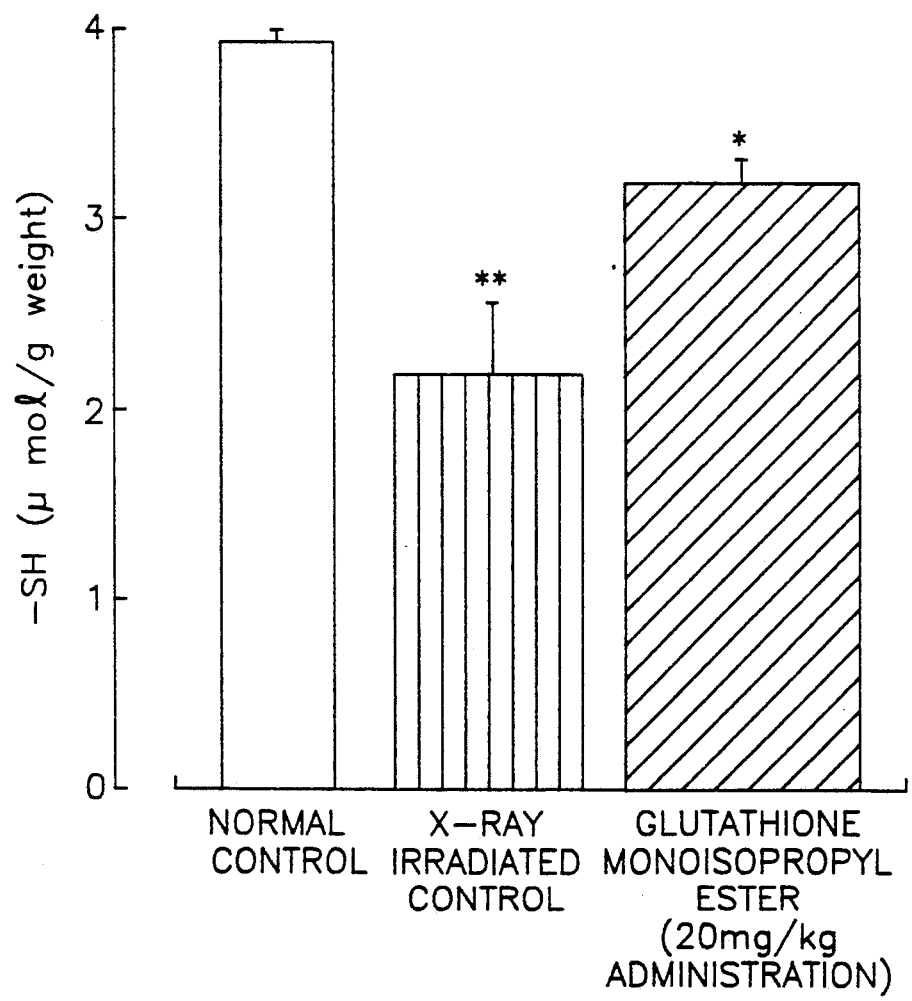
FIGS. 2(a), (b), and (c) show results of biochemical analysis of the glutathione monoisopropyl ester sulfate.
Figure 2:
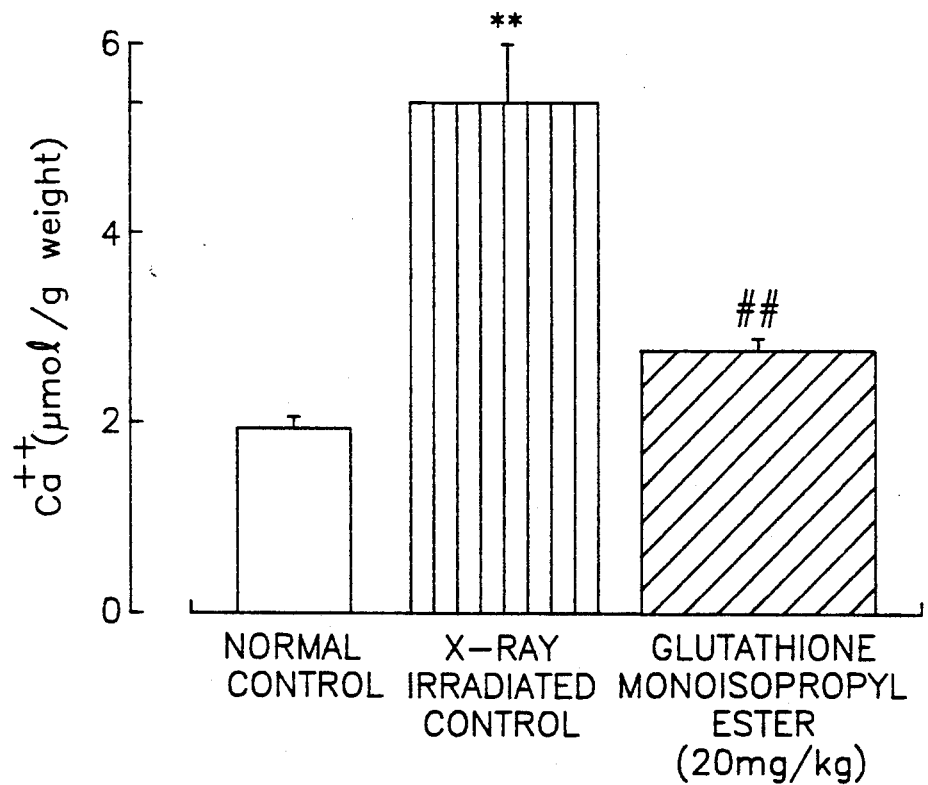

As indicated above, the present invention relates to prophylactic and therapeutic agents for cataracts comprising glutathione monoalkyl esters of general formula (I) or salts thereof as an effective component and a pharmaceutically acceptable carrier. Further, the present invention relates to radiation-protecting agents comprising glutathione monoalkyl ester of general formula (I) or salts thereof as an effective component and a pharmaceutically acceptable carrier.

In the formula (I), the alkyl group for the R radical is a straight or branched group of 1 to 10 carbon atoms. Specific examples thereof include methyl, ethyl, propyl, isopropyl, butyl, isobutyl, tert-butyl, pentyl, isopentyl, neopentyl, 1-methylbutyl, hexyl, isohexyl, 2-methylpentyl, 1-ethylbutyl, heptyl, octyl, nonyl, and decyl group, etc. Examples of the salts thereof include inorganic salts such as hydrochloride, nitrate, sulfate, etc., and organic salts such as oxalate, p-toluenesulfonate, maleate, and the like.

The glutathione monoalkyl esters of general formula (I) such as the glutathione monoisoproyl ester (isopropyl α-L-glutayl-L-cysteinylglycinate) sulfate are prepared according to the method described in the examples.

The glutathione monoalkyl ester or salts thereof, in accordance with the present invention, can be administered to a host, subject or patient in combination with pharmaceutically acceptable carriers for medical preparations, as well as excipients and other additives, which are conventionally employed. They can be simultaneously orally or parenterally. They are preferred administered parenterally in the form of injectable preparations, eye-drops, and the like.

The dose is about 10 mg to about 1,600 mg per person for injectable preparations, and about 1 to about 2% by weight in solution for eye-drops. Also the frequency of administration is commonly about one to three times daily and it is desirable that the preparation is formulated so as to comply with the above-mentioned conditions.

The compounds of the general formula (I) or salts thereof in accordance with the present invention have acute toxicity ($LD_{50}$) of approximately 5.3 g/kg in intraperitoneal injection to mice, for example, in the case of the isopropyl ester.

The invention will be more readily understood by reference to the drawings, wherein FIG. 1 represents an inhibiting action of a decrease in the amount of SH in lens, which was induced by X-ray radiation, 2c represents an inhibiting action of the increase of the $Na^+/K^+$ level in lens, which was induced by X-ray radiation, and 2c represents an inhibiting action of the increase of $Ca^{++}$ level in lens, which was induced by X-ray radiation.

The therapeutic effects for cataracts utilizing the effective component in accordance with the present invention are described hereinafter. The glutathione monoisopropyl ester (isopropyl-γ-L-glutamyl-L-cysteinylglycinate) sulfate used in the following experiments is prepared according to the method described in Example 1.

The following examples are illustrative.

EXAMPLE 1

Preparation of the Glutathione Monoisopropyl Ester

Example 1

To a mixture of 124 g glutathione and 800 ml isopropanol was added dropwise 42 ml of 95% sulfuric acid with stirring. The reaction was exothermic, but there was no need for external cooling. The mixture turned clear in about one hour, sulfate of glutathione monoisopropyl ester (isopropyl -L-glutamyl-L-cysteinyl-glycinate) began to separate out as crystals in about 24 hours, and stirring was further continued overnight. The crystals which separated out were collected by filtration, washed with 200 ml isopropanol and vacuum dried, giving 88.5 g of crude product.

(1) Part of the crude crystals collected above were recrystallized from a mixture of water and isopropanol (1:5), and the pure crystals thus obtained were submitted to analysis.

(i) M.p. 145°-150° C.

(ii) Elemental analysis (as $C_{13}H_{23}N_3O_6S \cdot \frac{1}{2}H_2SO_4 \cdot \frac{1}{2}H_2O$)

|  | C | H | N | S |
|---|---|---|---|---|
| Calcd. (%) | 38.32 | 6.18 | 10.31 | 11.80 |
| Found (%) | 38.11 | 6.34 | 10.32 | 12.10 |

(2) The crude crystals of sulfate collected above (5.0 g) were dissolved in 20 ml of a water/ethanol mixture (1:1) by heating at 80° C. for five minutes, and the solution was filtered and cooled on ice. The crystals which separated out were collected by filtration 60 minutes later, washed with 10 ml ethanol and vacuum-dried, affording 4.4 g of pure crystals of sulfate.

(i) M.p. 148°-150° C.

(ii) $[\alpha]^{20}_D - 15.5$ (c=1.0, $H_2O$)

(iii) Elemental analysis (as $C_{13}H_{23}N_3O_6S \cdot \frac{1}{2}H_2SO_4 \cdot \frac{1}{2}H_2O$)

|  | C | H | N | S |
|---|---|---|---|---|
| Calcd. (%) | 38.32 | 6.18 | 10.31 | 11.80 |
| Found (%) | 38.37 | 6.06 | 10.14 | 11.78 |

(iv) Mass spectrum: FAB: 350

(v) NMR spectrum (DMSO-$d_6$, $\delta$):

1.20 (6H, d, J=6 Hz) 1.7614 2.16 (2H, m)
2.20-2.48 (2H, m) 2.60-2.96 (2H, m)
3.48-3.72 (1H, m) 3.78 (2H, d, J=6 Hz)
4.24-4.56 (1H, m) 4.72-6.12 (1H, m)

In a similar manner, other compounds encompassed by formula (I) above can be prepared. See also U.S. Pat. No. 4,709,013.

EXAMPLE 2

Therapeutic Effect for Cataracts

Four-week old SLC Wistar rats are divided into three groups having ten animals in each group; the first group is a normal control group. The second group is an X-ray irradiated control group which is administered intraperitoneally 1 ml/kg of physiological saline solution three times a week after X-ray irradiation. For the third group, 20 mg/kg of glutathione monoisopropyl ester sulfate is administered intraperitoneally three times a week after X-ray irradiation. X-ray irradiation is carried out by irradiating the cephalic portion of conscious rats at 1,000 rad.

After X-ray irradiation, the lens are monitored every two weeks for opacity with a slit lamp. The apparent views of cataracts induced by X-ray radiation are scored using seven grades ranging from I and VII [from "clear" (namely, no change in the apparent view and substantially the same conditions as the normal control group) to "occurred opacitas"]. When the conditions of lens of the X-ray irradiated control group (the second group) reaches level IV or more (at 28 weeks), the tests are finished. Then the lens are extracted and measured for biochemical parameters [amounts of nonprotein-SH (Ellman's method), amounts of Na+/K+ and Ca++ (Atomic absorption method)].

The scoring results for the lens with X-ray induced cataracts, which are obtained with a slit lamp, are shown in FIG. 1. The therapeutic effects of glutathione monoisopropyl ester sulfate (the results of biochemical analysis) are shown in FIGS. 2a and 2c.

From the results in which the V grade is greater than 50% in the X-ray irradiated control group (the second group), while the II grade is greater than 50% in the glutathione monoisopropyl ester sulfate group (the third group, 20 mg/kg), it is evident that the ester exhibits an outstanding inhibiting action of cataracts.

EXAMPLE 3

Formulation of Eye-Drop Solution

The tablet containing 100 mg of glutathionemonoisopropyl ester sulfate was dissolved in a solution of 0.45 mg of benzalkonium chloride and 35 mg of boric acid, and the resulting mixture is shaken gently to obtain a transparent, colorless eye-drop solution.

From the foregoing experimental results, it is noted that the pharmaceutical preparations containing as an effective component the compounds of general formula (I) or salts thereof in accordance with the present invention exhibit a significant inhibiting action on the opacity of the lens of rats induced by X-ray radiation, upon intraperitoneally administering 20 mg/kg three times a week for 28 weeks. Accordingly, the pharmaceutical preparation containing the compounds of general formula (I) or salts thereof as an effective component is also considered to be sufficiently effective in the prophylaxis of X-ray-induced cataracts in humans. It is presumed that the mechanism of these anti-cataract effects results from the scavenger action of free radicals.

Further, senile cataracts of humans is histologically similar to X-ray induced cataracts and results from the existence of free radicals, which is one of triggers inducing senile cataracts. Thus, it can be said that the pharmaceutical preparation containing the compounds of general formula (I) or salts thereof as an effective component is useful for the prophylaxis and treatment of senile cataracts.

What is claimed is:

1. A method for the treatment of cataracts in a host which comprises administering to said host a cataract-inhibiting effective amount of a compound of the formula:

or a salt thereof, wherein R represents an alkyl group and a pharmaceutically acceptable carrier.

2. The method of claim 1, wherein R represents a lower alkyl group.

3. The method of claim 1, wherein R represents an isopropyl group.

* * * * *